(12) United States Patent
Lashmore et al.

(10) Patent No.: US 10,810,868 B2
(45) Date of Patent: Oct. 20, 2020

(54) INFRARED TEXTILE TRANSMITTER

(71) Applicant: American Boronite Corporation, Burlington, MA (US)

(72) Inventors: David S. Lashmore, Lebanon, NH (US); Pavel Bystricky, Lexington, MA (US); William Livernois, Cambridge, MA (US); Brandon Wilson, Somerville, MA (US)

(73) Assignee: American Boronite Corporation, Burlington, MA (US)

( * ) Notice: Subject to any disclaimer, the term of this patent is extended or adjusted under 35 U.S.C. 154(b) by 0 days.

(21) Appl. No.: 16/511,980

(22) Filed: Jul. 15, 2019

(65) Prior Publication Data

US 2020/0020224 A1    Jan. 16, 2020

Related U.S. Application Data

(60) Provisional application No. 62/697,848, filed on Jul. 13, 2018.

(51) Int. Cl.
*G08C 23/04* (2006.01)
*G08C 23/02* (2006.01)
*G01N 33/36* (2006.01)

(52) U.S. Cl.
CPC .......... *G08C 23/04* (2013.01); *G01N 33/362* (2013.01); *G01N 33/365* (2013.01); *G01N 33/367* (2013.01); *G08C 23/02* (2013.01); *D10B 2101/122* (2013.01)

(58) Field of Classification Search
CPC ...... G08C 23/04; G08C 23/02; G01N 33/362; G01N 33/365; G01N 33/367; D10B 2101/122

USPC .......................................................... 398/130
See application file for complete search history.

(56) References Cited

U.S. PATENT DOCUMENTS

| | | | | |
|---|---|---|---|---|
| 5,597,649 | A | * | 1/1997 | Sandor ..................... D01F 1/10 428/370 |
| 8,421,327 | B2 | | 4/2013 | Wei et al. |
| 8,801,487 | B2 | | 8/2014 | Wei et al. |
| 9,944,529 | B2 | | 4/2018 | Zhang et al. |

(Continued)

OTHER PUBLICATIONS

Li et. al., "Polarized incandescent light emission from carbon nanotubes," Applied Physics Letters vol. 82, No. 11, 4 page (date unavailable).

(Continued)

*Primary Examiner* — Dalzid E Singh
(74) *Attorney, Agent, or Firm* — Hamilton, Brook, Smith & Reynolds, P.C.

(57) ABSTRACT

Fiber emitters, such as carbon nanotube (CNT) yarns, are used to create infrared (IR) transmitters that can operate at high data rates, can shift spectral response, and can emit polarized light, for example by alignment of the fiber emitters in close proximity and in parallel directions. These fiber emitters can, for example, be used in patches that can be bonded to fabric or to an object, or can be woven into fabric during fabrication of a textile. The fiber emitters can be used in a variety of methods, including for friend or foe identification, communications, and identification of objects.

35 Claims, 14 Drawing Sheets
(12 of 14 Drawing Sheet(s) Filed in Color)

(56) References Cited

U.S. PATENT DOCUMENTS

| | | | |
|---|---|---|---|
| 2005/0095938 A1* | 5/2005 | Rosenberger | A41D 31/00 |
| | | | 442/194 |
| 2008/0170982 A1* | 7/2008 | Zhang | B82Y 10/00 |
| | | | 423/447.3 |
| 2010/0055352 A1* | 3/2010 | Maxwell | B81C 99/0095 |
| | | | 427/596 |
| 2011/0036828 A1* | 2/2011 | Feng | H05B 3/342 |
| | | | 219/529 |
| 2013/0137324 A1 | 5/2013 | Tang | |
| 2016/0222536 A1* | 8/2016 | Schauer | C25F 1/00 |
| 2016/0376747 A1* | 12/2016 | Wang | D03D 1/00 |
| | | | 428/335 |
| 2017/0196275 A1* | 7/2017 | Tam | A41D 31/065 |
| 2018/0240396 A1* | 8/2018 | Fontecchio | G09F 9/30 |
| 2019/0186059 A1* | 6/2019 | Yamamoto | D03D 15/00 |
| 2019/0225317 A1* | 7/2019 | Vincitore | B64C 1/18 |

OTHER PUBLICATIONS

Liu et. al., "Controlled Growth of Super-Aligned Carbon Nanotube Arrays for Spinning Continuous Unidirectional Sheets with Tunable Physical Properties," Nanoletters, 2008, vol. 8 No. 2, 11 pages.
M. Menat, "Applied Filter Radiometry," Infrared Physics, 1971, vol. 11, pp. 133-146. Hamamatsu Solid State Division, Technical Information SD-12, Characteristics and Use of Infrared Detectors.
A.S. Wu et al., "Strain rate-dependent tensile properties and dynamic electromechanical response of carbon nanotube fibers," Carbon, 50, 3876-3881 (2012).
Lin Xiao et al., "High frequency response of carbon nanotube thin film speaker in gases", Journal of Applied Physics 110, 084311 (2011), 6 pages.

* cited by examiner

INFRARED TEXTILE TRANSMITTER

RELATED APPLICATION

This application claims the benefit of U.S. Provisional Application No. 62/697,848, filed on Jul. 13, 2018. The entire teachings of the above application are incorporated herein by reference.

BACKGROUND

There is an ongoing need to provide solutions for communications in a variety of defense, security and high-value object contexts, including for "friend or foe" detection, communications with drones, satellites and aircraft, and for anti-counterfeiting applications, among others.

SUMMARY

In accordance with an embodiment of the invention, fiber emitters, such as carbon nanotube (CNT) yarns, are used to create infrared (IR) transmitters that can operate at high data rates, can shift spectral response, and can emit polarized light, for example by alignment of the fiber emitters in close proximity and in parallel directions. These fiber emitters can, for example, be used in patches that can be bonded to fabric or to an object, or can be woven into fabric during fabrication of a textile. The fiber emitters can be used in a variety of methods, including for friend or foe identification, communications, and identification of objects.

In one embodiment according to the invention, there is provided an infrared optical transmitter. The transmitter comprises a fiber emitter configured to be coupled to a textile, and an electrical connector coupled to the fiber emitter and configured to electrically couple to a power source to resistively heat the fiber emitter to transmit an infrared optical signal.

In further, related embodiments, the fiber emitter may be woven into the textile, or the infrared optical transmitter may comprise a patch that includes the fiber emitter, the patch configured to be coupled to the textile. The fiber emitter may be substantially non-detectable on the textile in visible light, while the infrared optical signal is detectable in infrared light. The infrared optical transmitter may further comprise the power source. The fiber emitter may comprise a nanotube. The nanotube may comprise at least one of a carbon nanotube, a boron nitride nanotube, a boron carbo-nitride nanotube, and a boron nanotube. The fiber emitter may comprise at least part of a yarn or sheet comprising the at least one of the carbon nanotubes, the boron nitride nanotubes, the boron carbo-nitride nanotubes, and the boron nanotubes. The fiber emitter may comprise at least part of a carbon nanotube yarn. The fiber emitter may comprise a carbon fiber. The fiber emitter may comprise a metal fiber, such as a tungsten fiber having a diameter between 2 and 4 microns. The fiber emitter may comprise a diameter between 1 micron and 50 microns; and may comprise a strength of at least 0.5 N/tex.

In other, related embodiments, the fiber emitter may comprise one of a plurality of fiber emitters positioned in a signal emission pattern. The signal emission pattern may comprise at least two fiber emitters positioned parallel to each other. The signal emission pattern may comprise at least two fiber emitter pattern blocks, each of the at least two fiber emitter pattern blocks comprising a fiber emitter oriented in a polarization direction different from a polarization direction of another one of the at least two fiber emitter pattern blocks. The signal emission pattern may comprise a bar code pattern, or a two-dimensional code.

In further, related embodiments, the infrared optical transmitter may further comprise an electrical signal encoder operatively connected to at least one of the power source and the electrical connector of the infrared optical transmitter such that the fiber emitter is resistively heated to transmit the infrared optical signal as an encoded infrared optical signal. The electrical signal encoder may be configured to encode the infrared optical signal to be transmitted from the fiber emitter at a frequency between 0.1 Hz and 100 kHz. The electrical signal encoder may be configured to encode the infrared optical signal to be transmitted from the fiber emitter at an infrared peak wavelength between 700 nm and 14 microns, such as between 900 nm and 2 microns. At least a portion of the fiber emitter may extend through an opening in the infrared optical transmitter, such as a sealed chamber within the infrared optical transmitter. The electrical signal encoder may be operatively connected to the at least one of the power source and the electrical connector of the infrared optical transmitter such that the encoded infrared optical signal is encrypted in at least one of a frequency, one or more spatial dimensions, a polarization state, and a shifting spectral intensity in one or more spatial locations of the infrared optical signal. The transmitter may be configured to emit the infrared optical signal encoded based on temperature of at least two fiber elements.

In other, related embodiments, the infrared optical transmitter may comprise at least a portion of a uniform, a helmet, a module configured to be attached to an object for automated identification, a drone, a satellite, an aircraft and an anticounterfeiting system. The transmitter may be configured to emit the infrared optical signal to a drone or other vehicle whose receiver is focused on the transmitter. The infrared optical transmitter may further comprise a transponder configured to automatically transmit an identification signal to a remote location using the transmitter.

In another embodiment according to the invention, there is provided a method of identification of a target. The method comprises: transmitting a signal to obtain identification of a target; receiving, in response to the transmitted signal, an infrared optical signal transmitted using an infrared optical transmitter, the transmitter comprising: (i) a fiber emitter configured to be coupled to a textile; and (ii) an electrical connector coupled to the fiber emitter and configured to electrically couple to a power source to resistively heat the fiber emitter to transmit an infrared optical signal; and identifying a sender of the infrared optical signal based on the received infrared optical signal. The infrared optical transmitter may comprise any infrared optical transmitter taught herein.

In another embodiment according to the invention, there is provided a method of performing remote communications. The method comprises: transmitting a request signal to establish a communications link with a remote sender; and receiving an infrared encrypted signal from the remote sender, in response to the request signal, the infrared encrypted signal transmitted using an infrared optical transmitter, the transmitter comprising: (i) a fiber emitter configured to be coupled to a textile; and (ii) an electrical connector coupled to the fiber emitter and configured to electrically couple to a power source to resistively heat the fiber emitter to transmit an infrared optical signal. The infrared optical transmitter may comprise any infrared optical transmitter taught herein.

In another embodiment according to the invention, there is provided a method of identifying an object. The method comprises: positioning an oscillating magnetic field source over an infrared optical transmitter coupled to a textile, the infrared optical transmitter comprising a fiber emitter, thereby inducing heating of the fiber emitter to transmit an infrared optical signal from the fiber emitter; and identifying the object based on the infrared optical signal received from the fiber emitter. The infrared optical transmitter may comprise any infrared optical transmitter taught herein.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
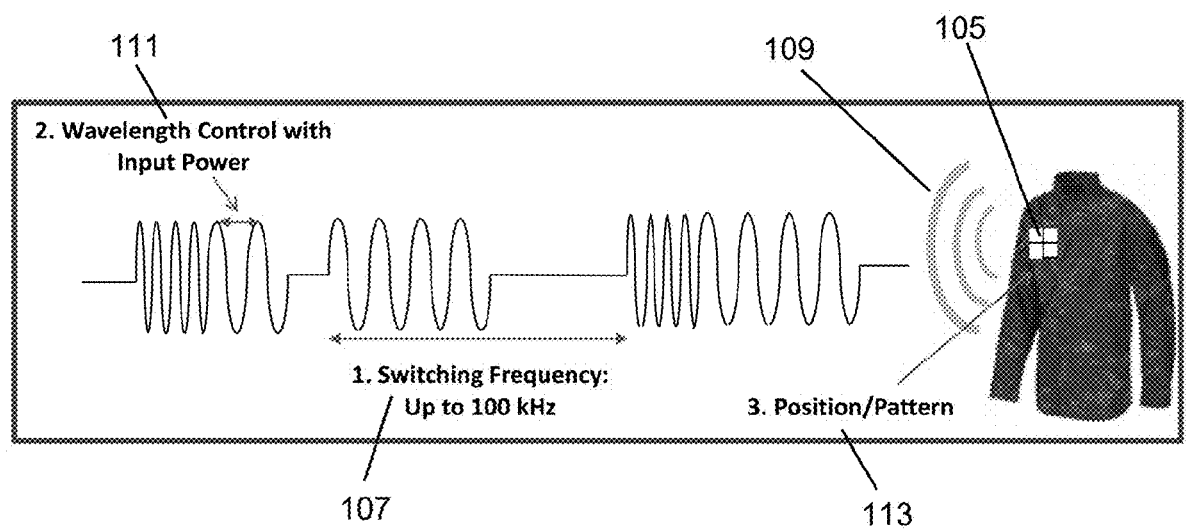
FIG. 1 is a schematic diagram illustrating use of an infrared optical transmitter comprising a fiber emitter, in accordance with an embodiment of the invention.

A description of example embodiments follows.

In accordance with embodiments of the invention, fiber emitters, such as carbon nanotube (CNT) yarns, can be used to create multispectral infrared (IR) encrypted data transmitters that can operate at high data rates, can shift spectral response, and can emit polarized light, for example by alignment of the fiber emitters in close proximity and in a parallel direction. Input to the yarn can, for example, be a sine or square wave pulsed at the same rate that the yarn is expected to heat and emit radiation. Data rates are determined by yarn size and by the material, if any, that the yarn is in contact with. Power requirements are determined by the yarn resistivity and the desired temperature.

These fiber emitters in accordance with embodiments of the invention, such as CNT transmitters, can for example be woven into fabric during fabrication of a textile, or can be created separately as a patch that can be bonded to fabric or an object. Creating a patch containing the fiber emitter can make it easier to separate the CNT or other fiber emitter from contact with anything that might slow down the data rates. Furthermore, CNT yarns can be used in true textiles that can be laundered and get dirty; and are strong and small enough that they can be woven or incorporated as patterned patches on textiles, or woven into existing fabrics, to create non-detectable patterns in visible light that are clearly detectable in infrared light. Their use in low volume makes this application very cost effective. The use of simple resistive heating element fiber infrared optical emitters, such as CNTs, that can, for example, operate at 0.1 MHz, in infrared optical transmitters taught herein, is surprising and unexpected. A property of CNT's that assists with such transmitters is the low specific heat of the CNT, which enables very fast heating and cooling rates when in minimal contact with other materials. The IR (optical) communications are not expected to be affected by electromagnetic pulse (EMP) interference. The transmitters can, for example, be: (1) woven into a military uniform or placed on a helmet or other equipment, (2) placed into modules that can be attached to objects for automated identification, (3) used to create a secure line of sight communications system between a drone and ground, between satellites or even within an aircraft, and used as (4) an anti-counterfeiting passive system on high value items. As will be discussed further below, this approach enables complex encryption in five dimensions: 1) frequency, 2) X dimension, 3) Y dimension (or other spatial dimensions), 4) polarization state and 5) spectral shift.

Secure line-of-sight communication requires (1) low power and (2) the ability to send secure information at high frequencies. The use of a continuously spun CNT yarn or other fiber emitter in accordance with an embodiment of the invention in a textile provides the ability to encrypt and transmit complex information at high rates even under poor weather conditions. High transmission rate depends on having little or no thermal contact between the yarn and the yarn mounting system and surrounding material, although it will be appreciated that a variety of different possible mounting systems and surrounding material can be used in accordance with teachings herein.

Small diameter carbon nanotube yarns have strengths that can vary from about 0.5 N/tex to over 3.1 N/tex. (1). These strengths far exceed those of common textile materials such as wool (0.15 N/tex) and Nylon (1 N/tex) and are comparable with Spectra® (3 N/tex), but without the loss of strength that comes from the effects of heat or humidity on polymeric fibers. In addition, the very small staple length of these fibers permits them to be tied in knots so that there is little, or no strength lost in weaving or due to fatigue. Carbon nanotube textiles in accordance with embodiments of the invention will survive dirt, laundering, acids, bleaches and other typical chemicals that textiles may be exposed to. The CNT yarns can also be blended into existing fabric patterns and made undetectable. There are, however, other fibers which can also be suitable. An example is carbon doped boron nitride nanotube yarn which, with the addition of carbon, becomes electrically conductive, has a very low specific heat and therefore can also be turned on and off very quickly. Another example is carbon fiber, which, while typically more resistive than CNT yarn, may nonetheless be used for this application. Normally, metal wires have too high a specific heat to be used at higher frequencies but at low frequencies some of these may also be suitable if they are extremely thin. For example, at low frequencies, a tungsten wire of diameter between 2 and 4 microns can be used. Other metal wires of diameter up to about 5 microns, for example, can be used.

In accordance with embodiments of the invention, fiber emitters include, for example, one or more of: a carbon nanotube (or CNT), a boron nitride nanotube (BNNT), a boron carbo-nitride nanotube (or BCN-NT), a boron nanotube (or BNT), a yarn (made from nanotubes), a tape or continuous nanotube tape, a sheet or continuous nanotube sheet, or high-quality nanotubes in bundle format.

Figure 5:
FIG. 5 is an example of a pattern that can be formed in a textile using a fiber emitter, in accordance with an embodiment of the invention.

In one embodiment, an encrypted data transmission device includes an IR sender based on a CNT small diameter (such as a diameter from 1 to 50 microns, for example about 10 microns) continuous CNT yarn (this normally means yarn continuously spun from a multitude of CNTs), and an IR receiver consisting of a diode or other IR detector/camera which in turn can have enhanced optics designed to maximize the signal to noise ratio and frequency response. The CNTs can be woven in any of a number of complex patterns: these can be parallel lines forming a linear barcode which can emit as a block with polarized radiation linked to the direction of the CNT placement on the textile. These blocks can also be combined together to create complex patterns such as a standardized 2D barcode, as shown in FIG. 5, or a wide range of custom patterns. Alternatively, the device can be concealed within areas of clothing that do not show any patterns that might reveal the CNT emitter under visible light. The signal output power affects detectability. Output power is related to the surface area radiating, temperature, and the atmospheric transmission conditions. Recently developed CMOS detectors/cameras that can detect approximately a single photon can, for example, be useful for this system. The distance between transmitter and receiver can be as much as kilometers apart and operate over a frequency ranging from a fraction of a Hz to up to 100 kHz depending on the environment and the diameter of the CNT yarn, and on the atmosphere/material in contact with the heated yarn. The optimized IR peak wavelength can, for example, range from 700 nm to 14 microns, such as preferably from 900 nm to 2 microns for an uncooled detector. In other examples, there can be used an infrared peak wavelength between 700 nm and 14 microns, such as between 900 nm and 2 microns; and further such as between any one of 1 micron to 1.4 microns, 3 microns to 5 microns or 8 microns to 14 microns. Note that the peak wavelength for IR emission from the human body is about 9.95 microns. As the distance between the source and receiver increases, the receiver may have to be a cooled InSb or HgCdTe detector (for example) and can be used with more complex optics. An embodiment according to the invention provides the capability of varying frequency from about 0.1 Hz to 100 kHz, thereby differing from light emitting diodes, which typically operate just at 38 kHz, and which are too large to be considered embeddable within a textile. Light emitting diodes also emit in discrete bands usually below 900 nm whereas an embodiment according to the invention provides emission up to 14 microns and over a broad range of frequencies, for example from 0.1 to 100 kHz.

In another embodiment, the CNT IR Pattern Emitter (CIRE) or other fiber emitter can be designed to emit an encrypted control signal to a drone whose receiver is always focused on the sender so that control can never be taken away (i.e., the control signal is resistant to jamming or spoofing).

In another embodiment, the CIRE or other fiber emitter can be linked to a transponder so that a "friend or foe" ID can be sent automatically by someone, or some system, to a transponder-receiver system located at some distance from the target soldier. For example, an interrogator (such as a sniper) can send out an RF signal, and a target soldier's IR device can send a series of codes in the infrared, using an infrared optical transmitter that includes a fiber emitter taught herein, which can be read by a detector by the sniper. Power for the system used can, for example, be supplied by a battery or a super capacitor system driven by a battery or by a solar cell array.

In another embodiment the CNT or other fiber emitter pattern can be passive, as opposed to other embodiments, which actively use a power source of their own. In one such embodiment, a fiber emitter (such as a CNT) is interrogated by an induced current produced by an oscillating magnetic field placed near the fiber emitter, camouflaged within a textile. Since the CNT is much more electrically conductive than the material it is embedded in, it will heat up by the induced current caused by the AC magnetic field, and the heat generated by each element on the pattern can be read by an IR camera or sensor system. One application of this is anti-counterfeiting for a wide variety of high value-added items, such as textiles, consumer goods, bearer bonds, currency, and in inventory control.

In another embodiment the CIRE or other fiber emitter can be placed within a structure such as an airplane and transmit information (control signals for example) to a receiver also located within the airplane. Such a device would not be affected by electromagnetic pulse (EMP) interference as much as RF transmitters.

FIG. 1 is a schematic diagram illustrating use of an infrared optical transmitter comprising a fiber emitter, in accordance with an embodiment of the invention. The figure depicts a summary of one example of how an encryption technique in accordance with an embodiment of the invention can be employed. CNT (or other fiber emitter) patches 105 woven into or placed in or on a uniform or other object can be caused to "light up" in the infrared, driven by an encoder connected to the textiles. The encoder can use a switching frequency 107 of, for example, up to 100 kHz. By controlling the input power delivered to the fiber emitter patches 105, which heats the fiber emitter to cause emission of the infrared optical signal 109, the wavelength of the infrared optical signal 109 can be controlled 111. The infrared optical signal 109 can also be varied based on the position and/or pattern 113 of the patches 105. The information transmitted can, for example, be encoded in position, in frequency and by modulating the IR wavelength and even by the state of polarization. The state of polarization can be selected by the direction in which parallel yarns are placed and which ones are caused to emit by the control system. Detection can, for example, be through an IR detector that may or may not be cooled. Most applications will require high detector performance and fast response in a narrow temperature range slightly above room temperature, meaning that such applications will require quantum detectors, such as PbS, Pb Se, InSb or HgCdTe, which will most likely require cooling for optimal sensitivity (4). The detector system can, for example, include one or more of a special filter, a thermoelectric cooler, or a Joule-Thomson cooler, and a carefully selected band pass filter. Alternatively, CMOS based visible/near IR detectors can be used. These detectors can include an IR array that creates a direct image in the IR.

Figure 2:
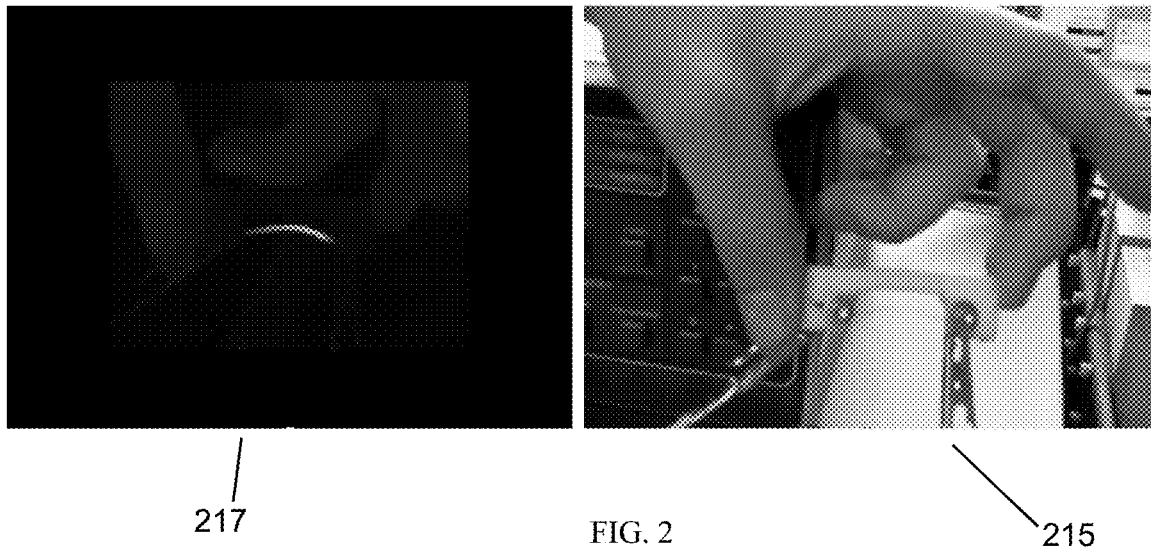
FIG. 2 is a photograph showing a static comparison in the visible image of a CNT yarn, in accordance with an embodiment of the invention, and a near-IR image of the same CNT yarn taken at the same time (same camera frame), in an experiment.

FIG. 2 is a photograph showing a static comparison in the visible image 215 of a CNT yarn, in accordance with an embodiment of the invention, and a near-IR image 217 of the same CNT yarn taken at the same time (same camera frame), in an experiment. In this example only one CNT thread has been placed. The CNT thread can be inserted into a textile pattern and is not detectable until the rapid current pulse, frozen in the video frame of the IR camera 217, is supplied. On/Off frequencies as high as 100 kHz have been reported under ideal circumstances, but these frequencies are limited by the diameter of the CNT wire or yarn in contact with surrounding material and the atmosphere in contact with the wire, and the characteristics of the receiver. This limitation is due to decreasing the heating and cooling rates of the CNT wire when it is in contact with another material.

Figure 3:
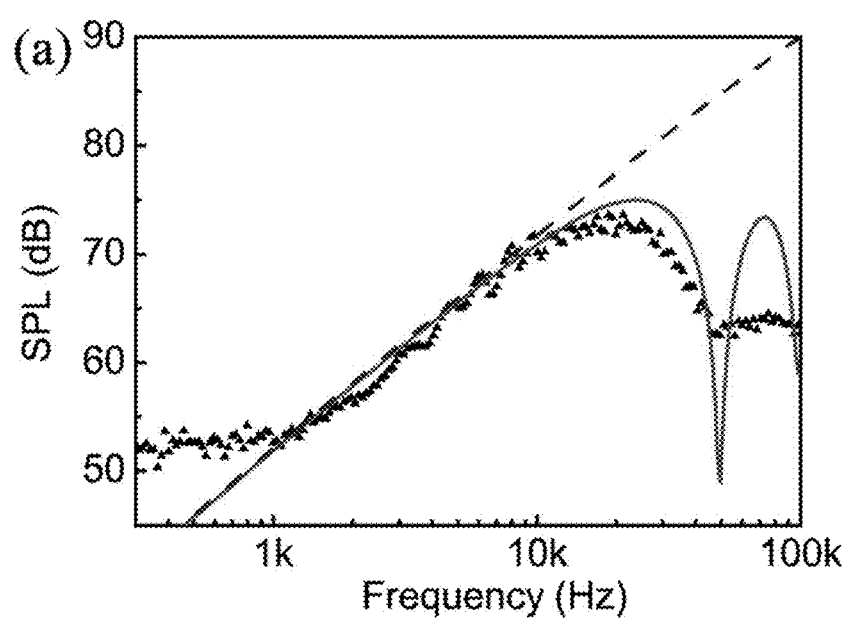
FIG. 3 is a graph of the predicted and measured frequency response of a CNT-based ultrasonic emitter showing that significant thermal energy is available at 100 kHz, in accordance with prior work, in which ultrasonic devices heat the air or gas adjacent to the CNT very quickly.

FIG. 3 is a graph of the predicted and measured frequency response of a CNT-based ultrasonic optical emitter showing that significant thermal energy is available at 100 kHz, in accordance with prior work, in which ultrasonic devices heat the air or gas adjacent to the CNT very quickly. (2). Based on such a graph, it is believed that significant thermal energy is available up to 100 kHz, for example, for embodiments according to the invention. The frequency response is of course a function of the environment, the length of the yarn and power level, so that short very thin nanotube structures will have a higher heating and cooling rate.

Figure 4:
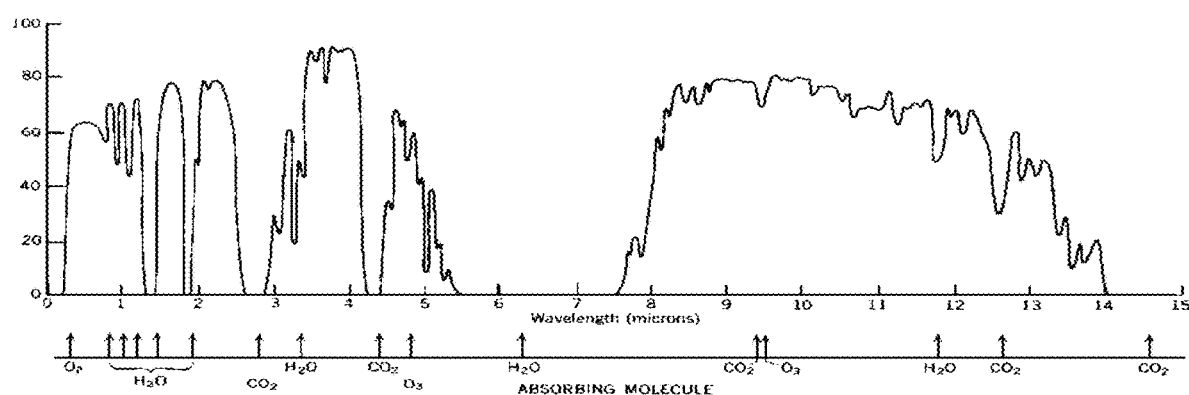
FIG. 4 is a very coarse atmospheric transmission spectrum at the surface of the earth considering a number of IR absorbing molecules, in accordance with the prior art.

FIG. 4 is a very coarse atmospheric transmission spectrum at the surface of the earth considering a number of IR absorbing molecules, in accordance with the prior art. The more important element in fog or bad weather is water. In an embodiment, the J band, 1 to 1.4 microns, is suggested, for example, for use as a peak wavelength of emission of an infrared optical transmitter. Operation can be improved with a cooled IR detector and/or operation in the 3 to 5-micron window, for example. The peak of emitted wavelength is determined by temperature. Analyzing the atmospheric transmission in the wavelength of interest and in the environment of interest will help improve the signal to noise ratio. Under some circumstances imaging in the 8 to 14-micron window of the atmosphere might be preferred for signals far away or near the background temperature.

In an embodiment, the receiver is carefully optimized so the sensor receiving the data will have the optimal signal to noise ratio as well as frequency response. This will, for example, likely require a sharp band-pass filter tailored to the expected atmospheric conditions. The function of this filter is to optimize signal to noise ratio by taking advantage of atmospheric windows and by filtering edges to transmit the signal and to remove unwanted background information. Commercial LED devices operate at short range and are not sensitive to atmospheric effects. When the distance (range) is extended, then transmission frequency selectivity of the receiver becomes very important. (3).

FIG. 5 is an example of a pattern that can be formed in a textile using a fiber emitter, in accordance with an embodiment of the invention. This pattern is one of a wide variety of patterns than can be formed from woven textiles. In this case it spells out in the two-dimensional non-polarized QR code: "Extraordinary materials for a demanding world".

Figure 6:
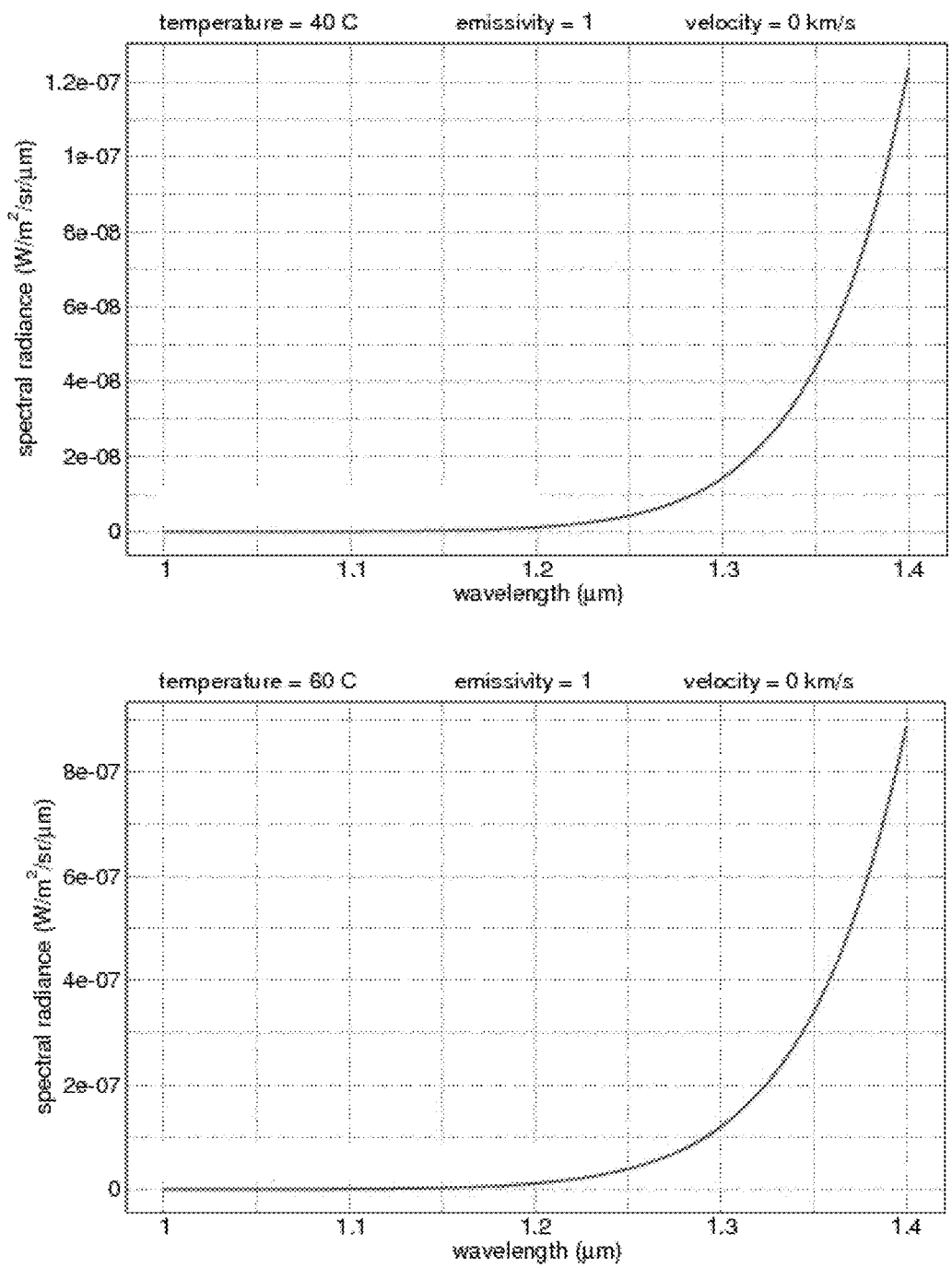
FIG. 6 is a set of graphs showing the low temperature spectral shift resulting from only a 20° C. increase in the temperature of the emitter, which shift can be used to encode information in accordance with an embodiment of the invention.

FIG. 6 is a set of graphs showing the low temperature spectral shift resulting from only a 20° C. increase in the temperature of the emitter, which shift can be used to encode information in accordance with an embodiment of the invention. In the example of FIG. 6, an increase of the temperature of the emitter from 40° C. (top graph) to 60° C. (bottom graph) results in an increase in peak spectral radiance at 1.4 micron wavelength, for example, from about $1.2 \times 10^{-7}$ $W/m^2/sr/\mu m$ to about $8 \times 10^{-7}$ $W/m^2/sr/\mu m$. CNT heater (or other fiber emitter) temperatures can be controlled from ambient temperature to over 1000° C., although textile applications will likely be close to body temperature. The CNTs are a good approximation of a black body. In one example, by creating pixel elements out of fiber emitters taught herein, and comparing a standard pixel element with another flashing at the same frequency, one can create a coded message based on temperature alone. In accordance with an embodiment of the invention, pixel elements or other heating elements can be created out of fiber emitters taught herein, and each pixel element can, for example, be flashed at various frequencies and can be polarized by orienting parallel arrays of thin yarns. Each pixel element can be spectrally shifted as well, enabling hierarchical encryption of increasing complexity. For example, Table 1 provides several possible kinds of encryption that can be used in accordance with embodiments of the invention.

TABLE 1

Types of Encryption

| Order of complexity | Type of Encryption | Discussion |
|---|---|---|
| 1 | By varying a heating element's turn-on/off frequency (period) | Simplest |
| 2 | By varying disposition of the heated elements in the X-direction or Y direction | For example, the elements can be uniformly placed in a pattern of from 1 to 5. The sequence 1, 3, 5, 2, 4 can then be lit up in order and in a specific frequency in the 1st |

TABLE 1-continued

Types of Encryption

| Order of complexity | Type of Encryption | Discussion |
|---|---|---|
| | | second and a different order at a different frequency in the $2^{nd}$ second etc. This can be done in two dimensions to provide very complex patterns which can be changed according to an agreed upon algorithm. |
| 3 | By varying polarization in different elements and turning single or groups of elements of one polarization on or off in a predetermined pattern. This single element would then be read through a polarizer. | This would require a rotating polarizer in the receiver to sync with the polarization frequency. |
| 4 | By varying the heating current to an element and measuring spectral shifting by passing the emitted radiation through a filter spectrometer. Alternatively, adjacent elements can be heated and cooled according to a pattern which can be verified by the detector and filter spectrometer. | By comparing a standard pixel element with another flashing at the same frequency one can create a coded message based on temperature which causes a spectral shift measured according to a standard element on the pattern. |

Figure 7A:
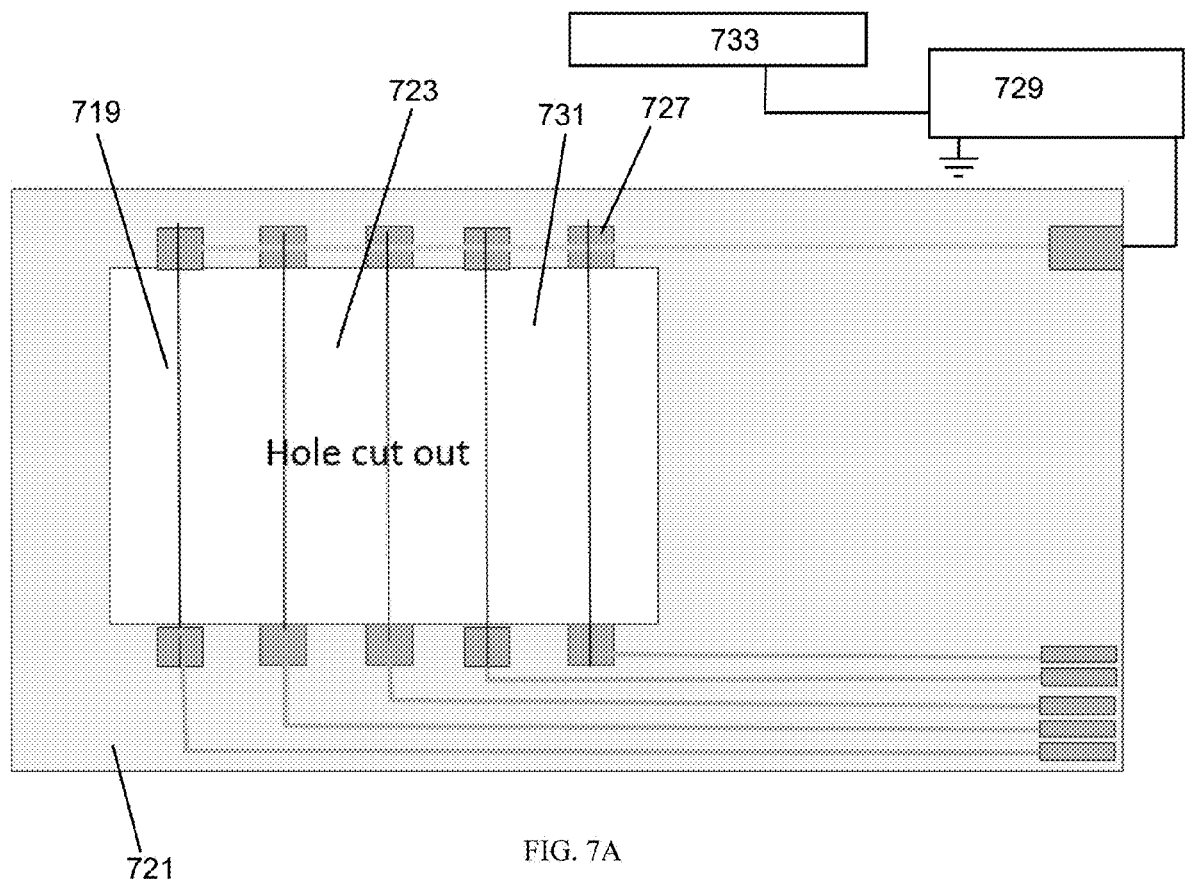
FIG. 7A is a top view schematic diagram of an infrared optical transmitter in accordance with an embodiment of the invention.
Figure 7B:
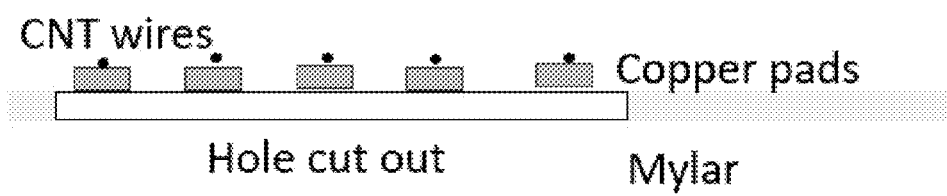
FIG. 7B is a side view schematic diagram of the infrared optical transmitter of FIG. 7A, in accordance with an embodiment of the invention.
Figure 9:
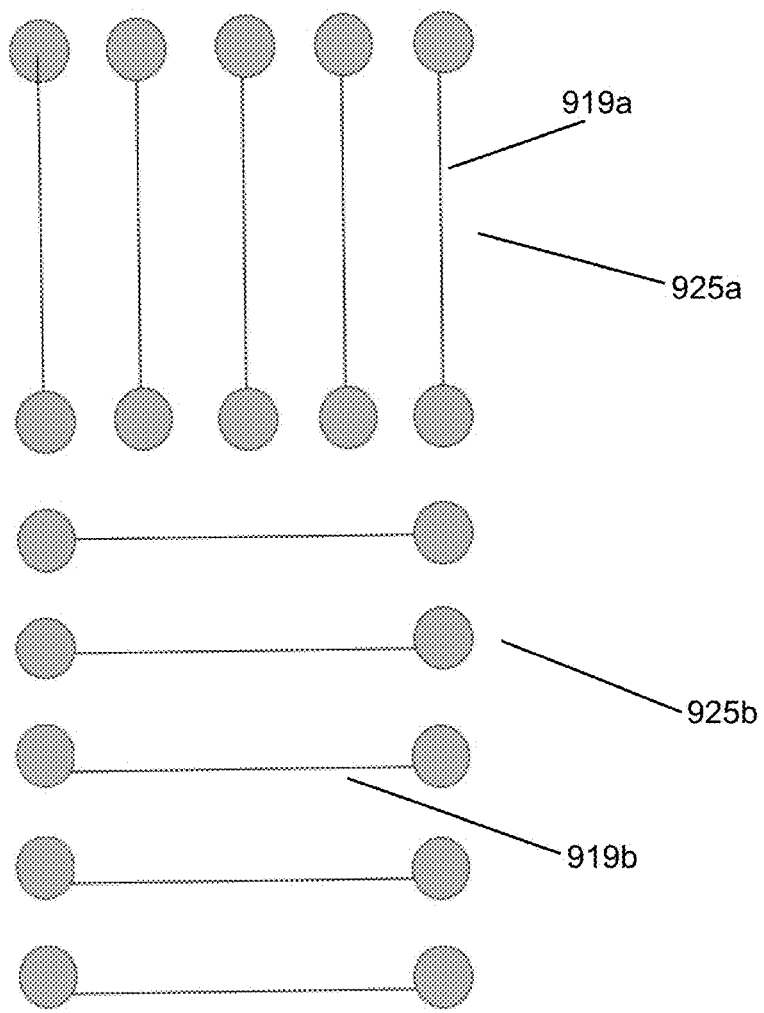
FIG. 9 is a schematic diagram of signal emission patterns of a pair of fiber emitter pattern blocks, in accordance with an embodiment of the invention.
Figure 10:
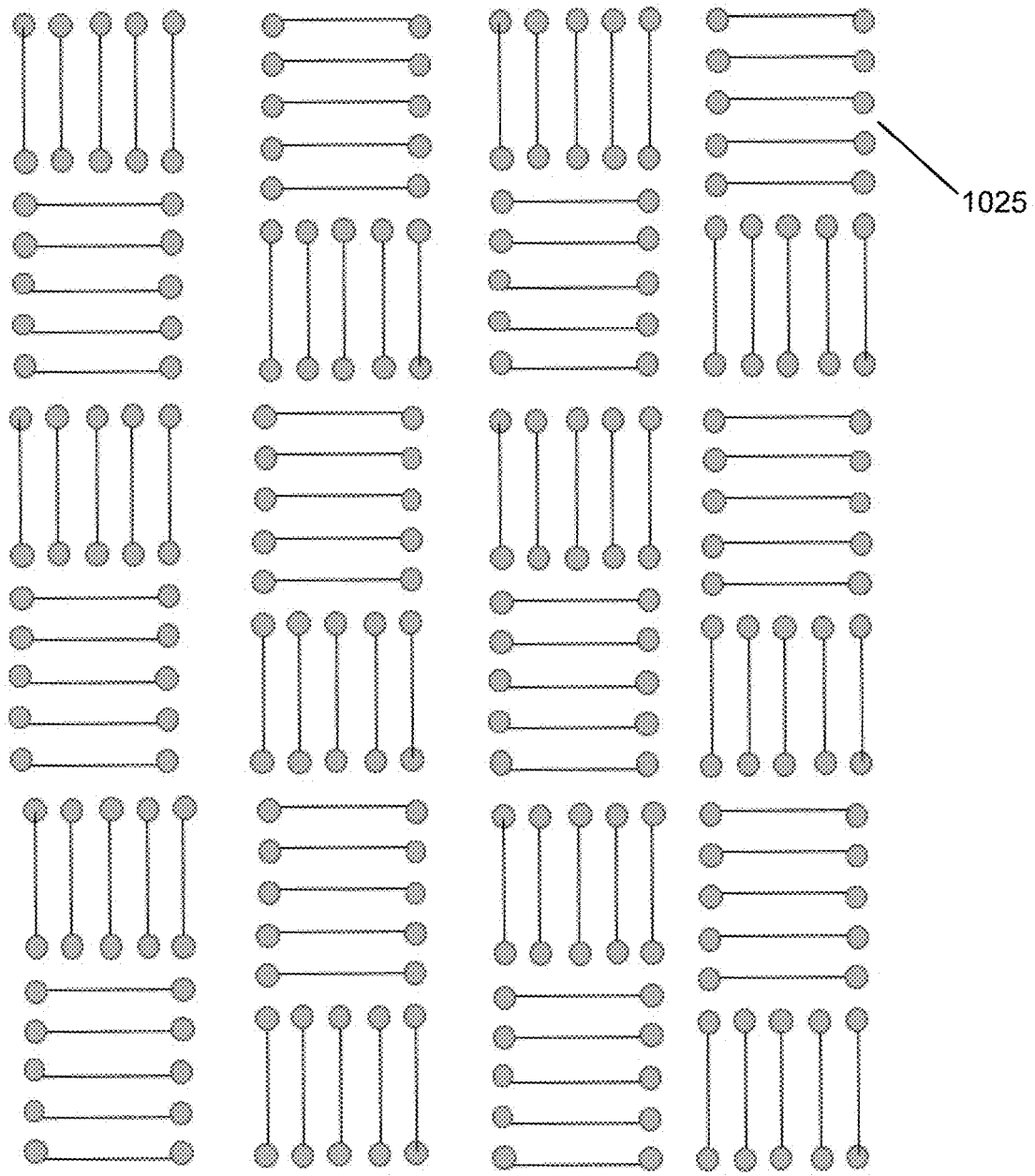
FIG. 10 is a schematic diagram of signal emission patterns of more than two fiber emitter pattern blocks, in accordance with an embodiment of the invention.

FIG. 7A is a top view schematic diagram of an infrared optical transmitter, and FIG. 7B is a side view schematic diagram of the infrared optical transmitter of FIG. 7A, in accordance with an embodiment of the invention. In this example, the infrared optical transmitter includes a fiber emitter 719 configured to be coupled to a textile. For example, in the example of FIGS. 7A and 7B, the fiber emitter 719 is configured to be coupled to a textile by comprising a part of a patch 721 that includes the fiber emitter 719, and the patch 721 is configured to be coupled to the textile, for example by being woven into, sewed onto, or adhered to the textile. The fiber emitter 719, in this example, is one of a plurality of fiber emitters positioned in a signal emission pattern 723, which in this case comprises five fiber emitters positioned parallel to each other. It will be appreciated that other signal emission patterns 723 can be used, such as a bar code pattern formed from the fiber emitters 719, or a two-dimensional code formed by the fiber emitters 719, such as the two-dimensional QR code of FIG. 5. In another example, FIG. 9 is a schematic diagram of signal emission patterns of a pair of fiber emitter pattern blocks 925a and 925b, in accordance with an embodiment of the invention. In this example, the signal emission pattern comprises two fiber emitter pattern block 925a, 925b, each of which comprises a fiber emitter 919a, 919b, oriented in a polarization direction different from the polarization direction of the other fiber emitter pattern blocks (in this case, in perpendicular polarization directions). In a further example, FIG. 10 is a schematic diagram of signal emission patterns of more than two fiber emitter pattern blocks 1025, in this case each oriented in one of two different polarization directions. Here, each signal emission pattern (or "block") can be caused to emit infrared radiation independently. It will be appreciated that a variety of other possible different arrangements and types of signal emission patterns can be formed from fiber emitters in accordance with an embodiment of the invention.

Returning to the embodiment of FIGS. 7A and 7B, the infrared optical transmitter further includes electrical connectors 727 coupled to the fiber emitters 719, which are configured to electrically couple to a power source 729 (which can be or include a power supply, battery, super capacitor system or other power source) to resistively heat the fiber emitter 719 to transmit an infrared optical signal. For example, the electrical connectors 727 can be copper (or another conductor). The patch 721 can, for example, be made of Mylar or polyamide, although it will be appreciated that a variety of flexible materials, textile materials, or other materials can be used as a substrate for the infrared optical transmitter. The fiber emitter 719 can, for example, be a CNT wire, or other fiber emitter taught herein. The fiber emitter 719 is bonded to the electrical connector 727, for example by bonding a CNT wire to a copper pad. The infrared optical transmitter can, for example, also include a protective cover (not shown). At least part of the fiber emitter 719 can extend through an opening 731 in the infrared optical transmitter, such as a hole cut out of the patch or other substrate. This can, for example, prevent thermal contact of the fiber emitter 719 with the surrounding textile or other substrate. The opening 731 can, for example, be a sealed chamber within the infrared optical transmitter, which can, for example, be filled with helium or another gas to increase data rates of transmission. The infrared optical transmitter can also include an electrical signal encoder 733, which is operatively connected to the power source 729 and/or the electrical connectors 727 so that the fiber emitter 719 is resistively heated to transmit an encoded infrared optical signal. For example, the encoder 733 can be configured to encode the infrared optical signal to be transmitted from the fiber emitter at any of the frequencies, wavelengths, or encoding techniques taught herein. The encoder 733 can, for example, be or include a dedicated digital signal processor, Application Specific Integrated Circuit (ASIC) or other circuit configured to encode using techniques taught herein to produce an electrical signal that drives the power source 729 accordingly to heat the fiber emitter 719 in a desired encoded fashion. In other embodiments, the encoder 733 can be or include, or be replaced by, a transponder that is configured to automatically transmit an identification signal to a remote location using the infrared optical transmitter.

Figure 8:
FIG. 8 is a schematic diagram illustrating spatial encoding based on fiber emitter positions, in accordance with an embodiment of the invention.

FIG. 8 is a schematic diagram illustrating spatial encoding based on fiber emitter positions, in accordance with an embodiment of the invention. In such spatial encoding, a complex encoding based on the fiber emitter positions can be used. In FIG. 8, there is shown a series of panels over time (here, times of 1 ms, 2 ms, 3 ms, 4 ms and 5 ms), at each of which times a different spatial pattern of activation of the fiber emitter positions is used, for example using encoder 733. For example, at time 1 ms, the second and fifth fiber emitters are activated, while the others are not activated, thereby producing a spatially observed pattern of (2, 5), meaning that second and fifth fiber emitters are activated. At 2 ms, the pattern of spatial activation of the fiber emitters is changed, to produce an observed pattern of (1, 5), and so on, with a pattern of (2, 3) at 3 ms, a pattern of (2, 5) at 4 ms, and a pattern of (2, 5) at 5 ms. In the right panel of FIG. 8, there is shown a time sequence (here, the 5 ms long burst) of the pulse train of the infrared optical signal emitted by the fiber emitters. This signal can be encrypted in any way by the encoder 733 (see FIG. 7). By heating one element more than another, as in FIG. 8, the ratio of detected signal at different wavelengths at different locations across the infrared optical transmitter is shifted. For example, at 1 ms, the pattern would show fiber emitters at spatial locations 2 and 5 emitting at a given wavelength, whereas, at 2 ms, the fiber emitters at spatial locations 1 and 5 would be emitting at such a wavelength (for example). Thus, a different pattern of spatial activation of the fiber emitters over time causes the ratios of signal intensities at different wavelengths to shift, spatially, for example from a pattern of (2, 5) to (1, 5) in spatial location across the five fiber emitters in FIG. 8. In operation, for example, one can measure the intensity of the line through a filter and the intensity of an adjacent line through a filter and take the ratios of the intensities. These ratios can be arbitrarily shifted to encode the shift e.g. the spectral shift.

Figure 11:
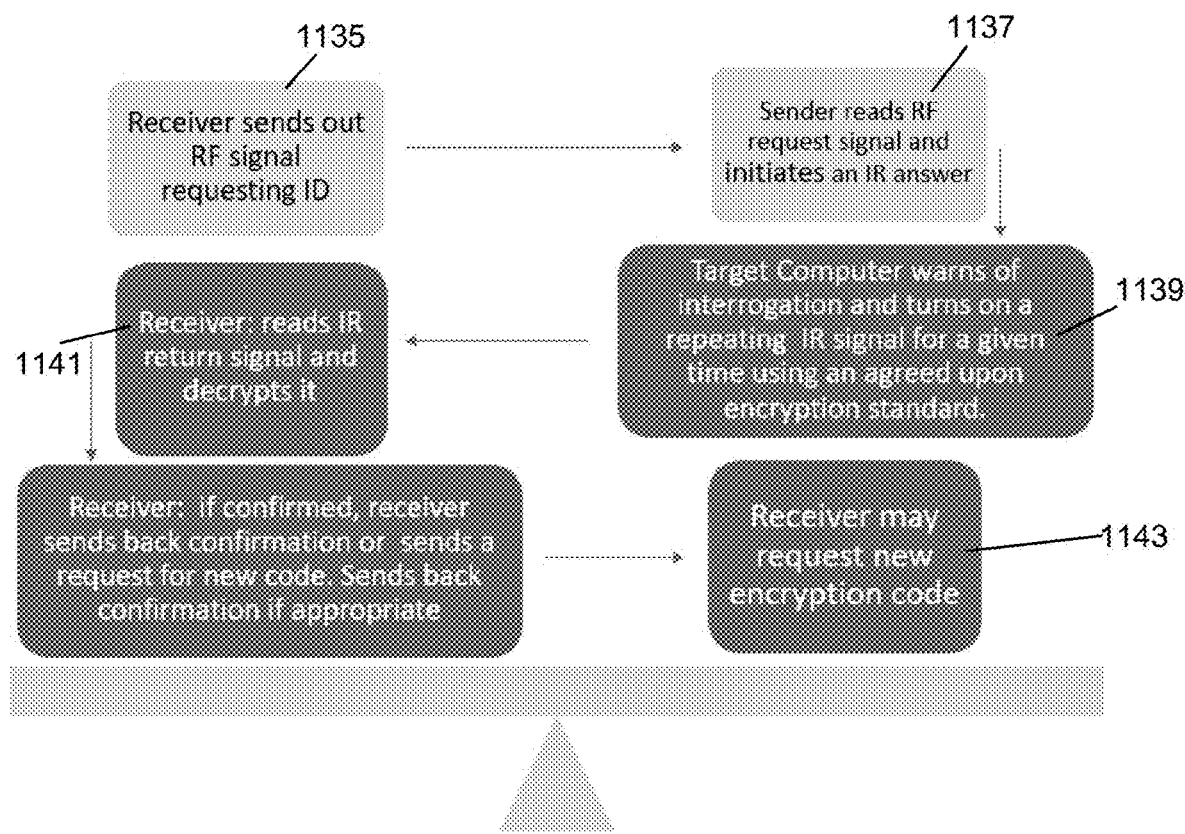
FIG. 11 is a schematic block diagram of a method of identification of a target, such as a method for "friend or foe" identification, in accordance with an embodiment of the invention.

FIG. 11 is a schematic block diagram of a method of identification of a target, such as a method for "friend or foe" identification, in accordance with an embodiment of the invention. Here, the method includes transmitting 1135 a signal to obtain identification of a target. For example, a receiver can send out an RF signal to request an ID. Next, a sender reads 1137 the RF request signal, and initiates an IR answer, using an infrared optical transmitter taught herein. For example, a target computer can warn of the interrogation, and turn on 1139 repeating IR signal for a given time, using an agreed-upon encryption standard. Next, the receiver receives 1141, in response to the transmitted signal, an infrared optical signal transmitted using an infrared optical transmitter taught herein. The method then includes identifying the sender of the infrared optical signal based on the received infrared optical signal. For example, the receiver can read the IR return signal 1141 and decrypt it; and, if confirmed, send back confirmation, or send a request for new code. The receiver can send back confirmation if appropriate. At 1143, it is shown that the receiver can request a new encryption code.

Figure 12:
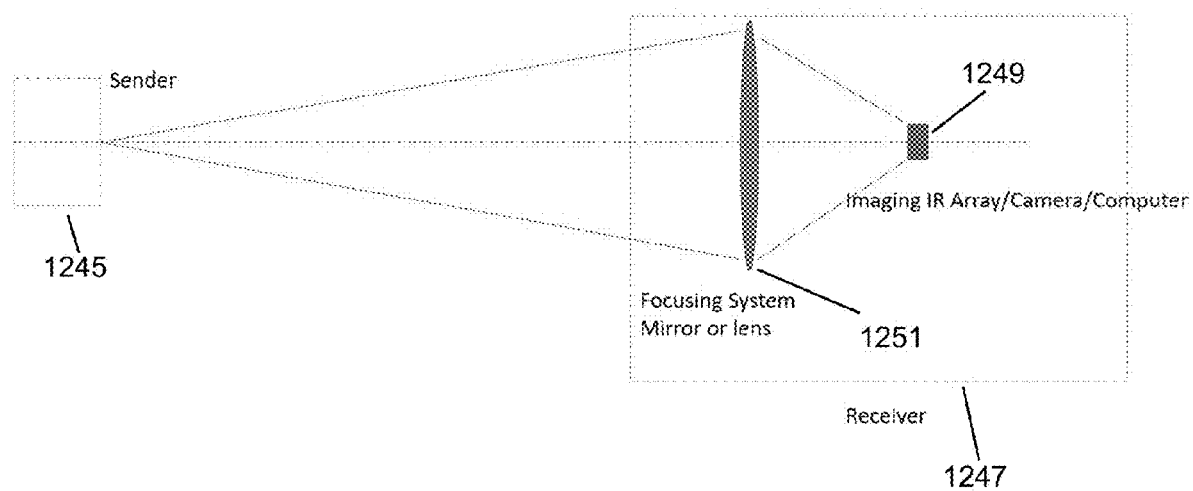
FIG. 12 is a schematic diagram illustrating a method of performing remote communications, in accordance with an embodiment of the invention.

FIG. 12 is a schematic diagram illustrating a method of performing remote communications, in accordance with an embodiment of the invention. In the method, it is assumed that the sender 1245 is small, the distance between the sender and receiver is large, and the receiver 1247 is small. The method comprising transmitting a request signal to establish a communications link with a remote sender 1245. For example, the request can be from a transponder (not shown in FIG. 12) of the receiver 1247. The sender 1245 then returns an IR encrypted signal to the receiver 1247, using an infrared optical transmitter taught herein. The IR image can be formed on an array 1249 and be analyzed by the receiver 1247 using a computer. The code can provide, for example, directional instructions, or request data to be sent from a remote source to the sender 1245. The receiver 1247 also can include a focusing system 1251, such as a mirror or lens.

Figure 13:
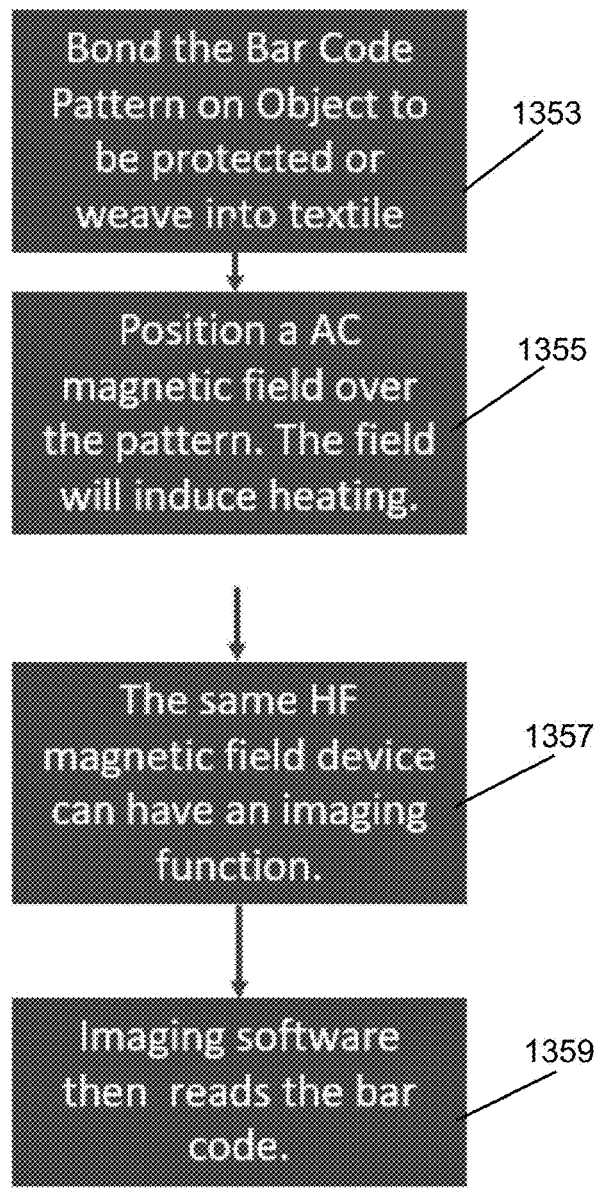
FIG. 13 is a schematic block diagram of a method of identifying an object, in accordance with an embodiment of the invention.

FIG. 13 is a schematic block diagram of a method of identifying an object, in accordance with an embodiment of the invention. In this method, a bar code pattern or other signal emission pattern made of fiber emitters taught herein is bonded 1353 on an object to be protected, for example, or woven into a textile. Then an AC magnetic field is positioned 1355 over the pattern. The field will induce heating. The same high frequency magnetic field device can have an imaging function 1357. The imaging software then reads 1359 the bar code pattern. The method thus includes positioning an oscillating magnetic field source over an infrared optical transmitter coupled to a textile, the infrared optical transmitter comprising a fiber emitter, thereby inducing heating of the fiber emitter to transmit an infrared optical signal from the fiber emitter; and identifying the object based on the infrared optical signal received from the fiber emitter.

Figure 14:
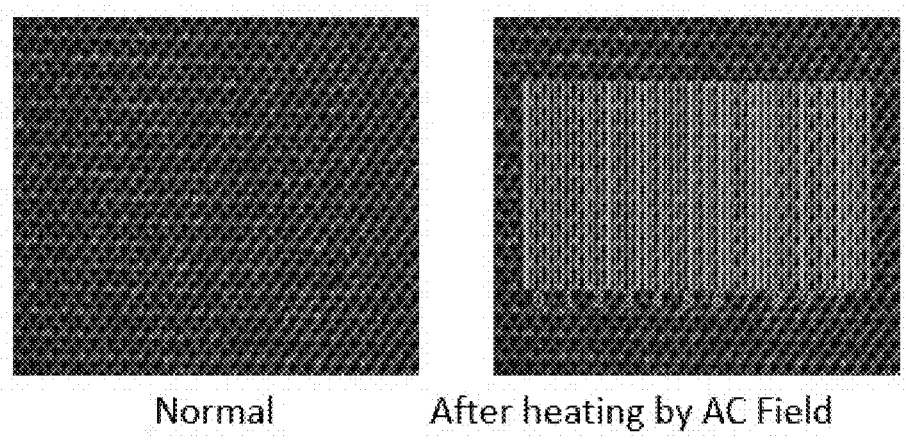
FIG. 14 is an example of a small bar code embedded in a textile using fiber emitters, in accordance with an embodiment of the invention.

FIG. 14 is an example of a small bar code embedded in a textile using fiber emitters, in accordance with an embodiment of the invention. In the left panel, the textile appears normal, but in the right panel, the bar code is revealed after heating by an AC field as in the embodiment of FIG. 13. Such an infrared textile transmitter can be embedded in a high value object and be made to warm up by an applied oscillating magnetic field that induces electric current in the transmitter to reveal an encrypted message or ID tag to be used, for example, for anti-counterfeiting. Such a passive (i.e., without an embedded power source) device may be embedded in a textile, object, currency, bearer bonds and the like. It can be bonded or sewn to the substrate. The bar code can, for example, be too small to see with the naked eye.

In one embodiment, a woven textile consisting of a CNT yarn of small diameter is inserted or woven into an existing textile or patch and used as a signaling device in the infrared. This signal can be encrypted in two (X, Y) dimensions, one dimension in frequency, and one dimension in wavelength of the infrared radiation. Operation can be at low temperatures where there is no visible emission. This signal can be polarized due to CNT alignment (another means of encryption). Examples of applications include: line of sight encrypted communications, friend or foe ID, drone control, encryption of valuable property.

In another embodiment, high frequency multispectral infrared emitters are created using CNT woven textiles. In one example, CNT patches woven into a uniform or other object can be caused to light up when driven by an encoder connected to a small power supply, such as a battery. The information can be encoded in position, in frequency and by modulating the IR wavelength, for example using the types of encryption in Table 1. Detection can be through a multichannel infrared radiometer with each channel set to a different frequency and a comparator chip to detect the encoding. Alternatively, detection can be with one detector, a curved focusing mirror and appropriate filters and encoders.

In one embodiment according to the invention, there is provided an infrared textile optical transmitter based on carbon nanotube yarns, or bundles or fibrils designed to produce IR emissions. The diameter of these textile emitters is between 1 micron and 100 microns, preferably 1 to 20 microns. This is far smaller than other available IR transmitters and smaller than LED devices embedded in hollow polymeric or glass fibers. The infrared textile transmitter can be designed to be used for line-of-sight communications that can, for example, be encrypted in two space dimensions, one dimension in frequency, one dimension of wavelength and one dimension of polarization. The encryption parameters can be changed in real time. The infrared textile optical transmitter can be used for a line-of-sight encrypted communication system between a controller and a receiver, such as, for example, a drone receiver. The infrared textile optical transmitter can be invisible in visible light and embedded on a military uniform, vehicle, tent, tank or other item to enable friend or foe ID from a suitably equipped receiver, for example mounted on a transponder equipped sniper scope. This transmitter can be a stand-alone patch sewn onto or bonded to an object.

In a further embodiment, an infrared textile transmitter is designed to have its peak intensity in near IR and optimized for the environment in which it is used to extend from 0.7 to 14 microns, or from 0.8 microns to 2 microns in the IR (or within the 3-5 micron atmospheric window or 8-14 micron window).

In another embodiment, a receiver is designed to detect the IR signal emitted by infrared optical transmitters taught herein. The receiver can, for example, consist of an optical chopper, a thermoelectric cooler, a photonic detector such as PbS or PbSe (InSb or HgCdTe) and a band-pass filter optimized for the wavelength of interest containing a transponder. The pattern can be placed onto or woven into, for example, a soldier's uniform.

As used herein, a "carbon nanotube" (or "CNT") can be thought of as a graphene plane rolled up into a tube capped with a half of a Bucky sphere at one end and usually a magnetic transition metal catalyst at the other. This graphene plane is characterized by $sp^2$ hybridized bonding which gives the surface its hexagonal symmetry, very good electronic properties, high strength, and a modulus of about 1 TPa and a unique Raman spectrum. These properties clearly distinguish CNTs from carbon fibers. Carbon nanotubes have a diameter range from about 0.8 nm to over 100 nm, typically ranging from about 1 to 10 nm. The length of these tubes spans from a few microns to many millimeters and occasionally to 20 or more centimeters. More typically they are about 1 or 2 millimeters in length. The tubes can be a single wall of graphene or dual wall or multiwalls. Very small diameter tubes, say less than 5 nm, are typically single walls. Depending on their structure (diameter and graphene plane configuration) they can conduct electricity as a metal or a semiconductor. They are black.

As used herein, a "boron nitride nanotube" (or "BNNT") is a well-ordered structure of alternating boron and nitrogen atoms forming a hexagonal plane rolled up into a tube.

As used herein, a "boron carbo-nitride nanotube" (or "BCN-NT"), can be thought of as BNNT in which some B and N atoms have been substituted with carbon atoms. The addition of carbon has profound effects on the electronic properties and color of the nanotubes. Increasing the relative proportion of carbon changes these materials from strong insulators at low (a few percent) carbon content to good conductors at high (for example 90%) carbon content. These are also nanotubes and have structures similar to CNTs and BNNTs. Their color is grey.

As used herein, a "boron nanotube" (or "BNT") is formed by a rolled-up sheet of buckled triangular arrangements of boron atoms or, alternatively, a modified hexagonal lattice in which some hexagons contain extra boron atoms, because a standard graphitic hexagonal lattice of B atoms is unstable. After relaxation, the surface of a BNT remains flat. Simulations predict most BNTs to be metallic regardless of chirality. Small carbon additions may increase stability and improve conductivity.

As used herein, a "yarn" (made from nanotubes) is a continuous strand of twisted nanotubes or bundles or fibrils of nanotubes, used in weaving or knitting textiles or as fiber reinforcement in composites or as electrical conductors. The yarns may be plied together to make larger fibers, wires or cables. The adhesion between the relatively short nanotubes (millimeters in length or less) derives from the surface interactions between tubes and from the twist imparting a capstan effect that increases frictional forces.

As used herein, a "tape" or "continuous nanotube tape" is usually a non-woven structure of nanotubes held together by electrostatic forces and by entanglement between the tubes. It can be produced in situ during growth or be cut from a large sheet and be bonded together with an adhesive to produce a continuous structure. The width of a tape can run from 0.5 cm to about 10 cm, its thickness can range from about 2 microns to about 200 microns, typically about 50 microns. Alternatively, tapes can be woven from aligned yarns.

As used herein, a "sheet" or "continuous nanotube sheet" is a wide tape produced in a batch system and bonded to another tape to constitute a continuous sheet (thousands of feet long) or it can be produced on a machine in a continuous manner. These structures are typically non-woven, their width ranges from about 10 cm to about 500 cm, their thickness ranges from about 2 microns to about 200 microns. Alternatively, continuous nanotube sheet or fabric can be woven from nanotube yarns in a manner known to the textile industry.

As used herein, "high-quality nanotubes" means nanotubes with a minimal number of structural or crystallographic defects, such as for example Stone-Wales defects. "Highly conductive nanotubes" means nanotubes with fewer than about one defect per micron whose length is larger than the mean free path of about 1 micron.

REFERENCES (1) A. S. Wu, X, Nie, M. C. Hudspeth, W. W. Chen, D. Lashmore, M. Schauer, E. Tolle and J. Rioux. "Strain rate-dependent tensile properties and dynamic electromechanical response of carbon nanotube fibers," *Carbon,* 50, 3876-3881 (2012).

(2) Lin Xiao, Peng Liu, Liang Liu, Qunqing Li, Zhenghe Feng, Shoushan Fan, and Kaili Jiang, "High frequency response of carbon nanotube thin film speaker in gases", Journal of Applied Physics 110, 084311 (2011).

(3) M. Menat, Applied Filter Radiometry, Infrared Physics, 1971, Vol. 11, pp. 133-146.

(4) Hamamatsu Solid State Division, Technical Information SD-12, *Characteristics and Use of Infrared Detectors.*

Kalli et. al., "Polarized incandescent light emission from carbon nanotubes," *Applied Physics Letters* Vol. 82, No. 11.

Liu et. al., "Controlled Growth of Super-Aligned Carbon Nanotube Arrays for Spinning Continuous Unidirectional Sheets with Tunable Physical Properties," *Nanoletters,* 2008 Vol 8 No. 2, 700-705.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An infrared optical transmitter, the transmitter comprising:
   a fiber emitter configured to be coupled to a textile;
   an electrical connector coupled to the fiber emitter and configured to electrically couple to a power source to resistively heat the fiber emitter to transmit an infrared optical signal; and
   an electrical signal encoder operatively connected to at least one of the power source and the electrical connector of the infrared optical transmitter such that the fiber emitter is resistively heated to transmit the infrared optical signal as an encoded infrared optical signal.

2. The infrared optical transmitter of claim 1, wherein the fiber emitter is woven into the textile.

3. The infrared optical transmitter of claim 1, comprising a patch that includes the fiber emitter, the patch configured to be coupled to the textile.

4. The infrared optical transmitter of claim 1, wherein the fiber emitter is substantially non-detectable on the textile in visible light, and wherein the infrared optical signal is detectable in infrared light.

5. The infrared optical transmitter of claim 1, further comprising the power source.

6. The infrared optical transmitter of claim 1, wherein the fiber emitter comprises a nanotube.

7. The infrared optical transmitter of claim 6, wherein the nanotube comprises at least one of a carbon nanotube, a boron nitride nanotube, a boron carbo-nitride nanotube, and a boron nanotube.

8. The infrared optical transmitter of claim 7, wherein the fiber emitter comprises at least part of a yarn or sheet comprising the at least one of the carbon nanotube, the boron nitride nanotube, the boron carbo-nitride nanotube, and the boron nanotube.

9. The infrared optical transmitter of claim 8, wherein the fiber emitter comprises at least part of a carbon nanotube yarn.

10. The infrared optical transmitter of claim 1, wherein the fiber emitter comprises a carbon fiber.

11. The infrared optical transmitter of claim 1, wherein the fiber emitter comprises a metal wire.

12. The infrared optical transmitter of claim 11, wherein the fiber emitter comprises a tungsten wire having a diameter between 2 and 4 microns.

13. The infrared optical transmitter of claim 1, wherein the fiber emitter comprises a diameter between 1 micron and 50 microns.

14. The infrared optical transmitter of claim 1, wherein the fiber emitter comprises a strength of at least 0.5 N/tex.

15. The infrared optical transmitter of claim 1, wherein the fiber emitter comprises one of a plurality of fiber emitters positioned in a signal emission pattern.

16. The infrared optical transmitter of claim 15, wherein the signal emission pattern comprises at least two fiber emitters positioned parallel to each other.

17. The infrared optical transmitter of claim 15, wherein the signal emission pattern comprises at least two fiber emitter pattern blocks, each of the at least two fiber emitter pattern blocks comprising a fiber emitter oriented in a polarization direction different from a polarization direction of another one of the at least two fiber emitter pattern blocks.

18. The infrared optical transmitter of claim 15, wherein the signal emission pattern comprises a bar code pattern.

19. The infrared optical transmitter of claim 15, wherein the signal emission pattern comprises a two-dimensional code.

20. The infrared optical transmitter of claim 1, wherein the electrical signal encoder is configured to encode the infrared optical signal to be transmitted from the fiber emitter at a frequency between 0.1 Hz and 100 kHz.

21. The infrared optical transmitter of claim 1, wherein the electrical signal encoder is configured to encode the infrared optical signal to be transmitted from the fiber emitter at an infrared peak wavelength between 700 nm and 14 microns.

22. The infrared optical transmitter of claim 21, wherein the electrical signal encoder is configured to encode the infrared optical signal to be transmitted from the fiber emitter at an infrared peak wavelength between 900 nm and 2 microns.

23. The infrared optical transmitter of claim 1, wherein at least a portion of the fiber emitter extends through an opening in the infrared optical transmitter.

24. The infrared optical transmitter of claim 23, wherein the opening comprises a sealed chamber within the infrared optical transmitter.

25. The infrared optical transmitter of claim 1, wherein the electrical signal encoder is operatively connected to the at least one of the power source and the electrical connector of the infrared optical transmitter such that the encoded infrared optical signal is encrypted in at least one of a frequency, one or more spatial dimensions, a polarization state, and a shifting spectral intensity in one or more spatial locations of the infrared optical signal.

26. The infrared optical transmitter of claim 1, wherein the transmitter is configured to emit the infrared optical signal encoded based on temperature of at least two fiber elements.

27. The infrared optical transmitter of claim 1, comprising at least a portion of a uniform, a helmet, a module configured to be attached to an object for automated identification, a drone, a satellite, an aircraft and an anticounterfeiting system.

28. The infrared optical transmitter of claim 1, wherein the transmitter is configured to emit the infrared optical signal to a drone or other vehicle whose receiver is focused on the transmitter.

29. The infrared optical transmitter of claim 1, further comprising a transponder configured to automatically transmit an identification signal to a remote location using the transmitter.

30. A method of identification of a target, the method comprising:
   transmitting a signal to obtain identification of a target;
   receiving, in response to the transmitted signal, an infrared optical signal transmitted using an infrared optical transmitter, the transmitter comprising: (i) a fiber emitter configured to be coupled to a textile; and (ii) an electrical connector coupled to the fiber emitter and configured to electrically couple to a power source to resistively heat the fiber emitter to transmit an infrared optical signal; and
   identifying a sender of the infrared optical signal based on the received infrared optical signal.

31. A method of performing remote communications, the method comprising:
   transmitting a request signal to establish a communications link with a remote sender; and receiving an infrared encrypted signal from the remote sender, in response to the request signal, the infrared encrypted signal transmitted using an infrared optical transmitter, the transmitter comprising: (i) a fiber emitter configured to be coupled to a textile; and (ii) an electrical connector coupled to the fiber emitter and configured to electrically couple to a power source to resistively heat the fiber emitter to transmit an infrared optical signal.

32. A method of identifying an object, the method comprising:

positioning an oscillating magnetic field source over an infrared optical transmitter coupled to a textile, the infrared optical transmitter comprising a fiber emitter, thereby inducing heating of the fiber emitter to transmit an infrared optical signal from the fiber emitter; and identifying the object based on the infrared optical signal received from the fiber emitter.

33. An infrared optical transmitter, the transmitter comprising:

a fiber emitter configured to be coupled to a textile; and an electrical connector coupled to the fiber emitter and configured to electrically couple to a power source to resistively heat the fiber emitter to transmit an infrared optical signal;

the fiber emitter comprising one of a plurality of fiber emitters positioned in a signal emission pattern, the signal emission pattern comprising at least one of:

(a) at least two fiber emitter pattern blocks, each of the at least two fiber emitter pattern blocks comprising a fiber emitter oriented in a polarization direction different from a polarization direction of another one of the at least two fiber emitter pattern blocks;

(b) a bar code pattern; and (c) a two-dimensional code.

34. An infrared optical transmitter, the transmitter comprising:

a fiber emitter configured to be coupled to a textile; and an electrical connector coupled to the fiber emitter and configured to electrically couple to a power source to resistively heat the fiber emitter to transmit an infrared optical signal;

wherein the transmitter is configured to emit the infrared optical signal encoded based on temperature of at least two fiber elements.

35. An infrared optical transmitter, the transmitter comprising:

a fiber emitter configured to be coupled to a textile;

an electrical connector coupled to the fiber emitter and configured to electrically couple to a power source to resistively heat the fiber emitter to transmit an infrared optical signal; and a transponder configured to automatically transmit an identification signal to a remote location using the transmitter.

* * * * *